United States Patent [19]

Spitzer et al.

[11] Patent Number: 5,258,325
[45] Date of Patent: Nov. 2, 1993

[54] METHOD FOR MANUFACTURING A SEMICONDUCTOR DEVICE USING A CIRCUIT TRANSFER FILM

[75] Inventors: Mark B. Spitzer, Sharon; Jack P. Salerno, Waban, both of Mass.; Jeffrey Jacobsen, Hollister, Calif.; Brenda Dingle, Mansfield, Mass.; Duy-Phach Vu, Taunton, Mass.; Paul M. Zavracky, Norwood, Mass.

[73] Assignee: Kopin Corporation, Taunton, Mass.

[21] Appl. No.: 834,849

[22] Filed: Feb. 13, 1992

Related U.S. Application Data

[63] Continuation-in-part of Ser. No. 636,602, Dec. 31, 1990, Pat. No. 5,206,749, and a continuation-in-part of Ser. No. 643,552, Jan. 18, 1991.

[51] Int. Cl.[5] ............... H01L 21/20; H01L 21/22; H01L 21/304; H01L 21/52
[52] U.S. Cl. .................... 437/86; 437/205; 437/208; 437/966; 437/974; 156/DIG. 88; 29/25.01
[58] Field of Search ............ 437/205, 208, 86, 966, 437/974; 156/DIG. 88

[56] References Cited

U.S. PATENT DOCUMENTS

| | | | |
|---|---|---|---|
| 3,658,618 | 4/1972 | Gramann | 437/205 |
| 4,226,649 | 10/1980 | Davey et al. | 437/86 |
| 4,255,208 | 3/1981 | Deutscher et al. | 156/DIG. 88 |
| 4,321,747 | 3/1982 | Takemura et al. | 437/974 |
| 4,575,854 | 3/1986 | Martin | 372/75 |
| 4,727,047 | 2/1988 | Bozler et al. | 437/89 |
| 4,769,680 | 9/1988 | Resor, III et al. | 355/43 |
| 4,774,205 | 9/1988 | Choi et al. | 437/59 |
| 4,837,182 | 6/1989 | Bozler et al. | 437/966 |
| 4,846,931 | 7/1989 | Gmitter et al. | 156/633 |
| 4,855,255 | 8/1989 | Goodhue | 156/633 |
| 4,863,877 | 9/1989 | Fan et al. | 437/22 |
| 4,871,517 | 10/1989 | Falckenberg et al. | 156/DIG. 88 |
| 4,883,561 | 11/1989 | Gmitter et al. | 156/633 |
| 4,979,002 | 12/1990 | Pankove | 357/17 |
| 4,980,308 | 12/1990 | Hayashi et al. | 437/41 |
| 5,045,895 | 9/1991 | Yoshida et al. | 357/17 |
| 5,073,806 | 12/1991 | Idei | 357/17 |

FOREIGN PATENT DOCUMENTS

| | | |
|---|---|---|
| 57-106181 | 7/1982 | Japan . |
| 61-280660 | 12/1986 | Japan ............ 437/205 |
| 63-55529 | 3/1988 | Japan . |
| 63-055529 | 10/1988 | Japan . |
| 64-38727 | 2/1989 | Japan . |
| WO90/09038 | 8/1990 | PCT Int'l Appl. . |
| WO91/02380 | 2/1991 | PCT Int'l Appl. . |

OTHER PUBLICATIONS

Milnes, A. G., "Semiconductor Heterojunction Topics: Introduction and Overview", *Solid State Electronics*, vol. 29, 2:99–121, (1986).

Akiyama, M. et al., "Growth of GaAs on Si and Its Application to FETs and LEDs", *Nat. Res. Soc. Symp. Proc.*, 67:53–64 (1986).

(List continued on next page.)

Primary Examiner—Olik Chaudhuri
Assistant Examiner—David E. Graybill
Attorney, Agent, or Firm—Hamilton, Brook, Smith & Reynolds

[57] ABSTRACT

The invention relates to device processing, packaging and interconnects that will yield integrated electronic circuitry of high density and complexity. Processes include the formation of complex multi-function circuitry on common module substrates using circuit tiles of silicon thin-films which are transferred, interconnected and packaged. Circuit modules using integrated transfer/interconnect processes compatible with extremely high density and complexity provide large-area active-matrix displays with on-board drivers and logic in modules.

28 Claims, 11 Drawing Sheets

OTHER PUBLICATIONS

Turner, G. et al., "High-Speed Photoconductive Detectors Fabricated in Heteroepitaxial GaAs Layers", *Mat. Res. Soc. Symp. Proc.*, 67:181-188 (1986).

McDaniel, D. L. et al., "Vertical Cavity Surface-Emitting Semiconductor Laser with CW Injection Laser Pumping", *IEEE Photon Technol. Lett.*, Mar. 23, 1990.

Weber, J. P. et al., "Effects of Layer Thickness Variations on Vertical Cavity Surface-Emitting DBR Semiconductor Lasers", IEEE Photon Tech. Ltr., Mar. 23, 1990.

"3-D Chip-On-Chip Stacking", *Semiconductor International*, Dec. 1991.

McClelland et al., "A Technique for Producing Epitaxial Films on Reusable Substrates", Appl. Phys. Lett. 37, 560, Sep. 15, 1980.

Yablonovitch et al., "Extreme Selectivity in the Lift-Off of Epitaxial GaAs Films", *Appl. Phys. Lett.* 51, 2222 Dec. 28, 1987.

Fan et al., "Lateral Epitaxy by Seeded Solidification for Growth of Crystal Si Films on Insulators", Appl. Phys. Lett., 38, 365, Mar. 1 1981.

Allen et al., "Characterization of Isolated Silicon Epitaxy Material", SPIE vol. 945-Advanced Processing of Semiconductor Devices II (Mar. 17-Mar. 18, 1988).

Conference Record of the 1991 International Display Research Conference, Oct. 15-17, 1991, IEEE.

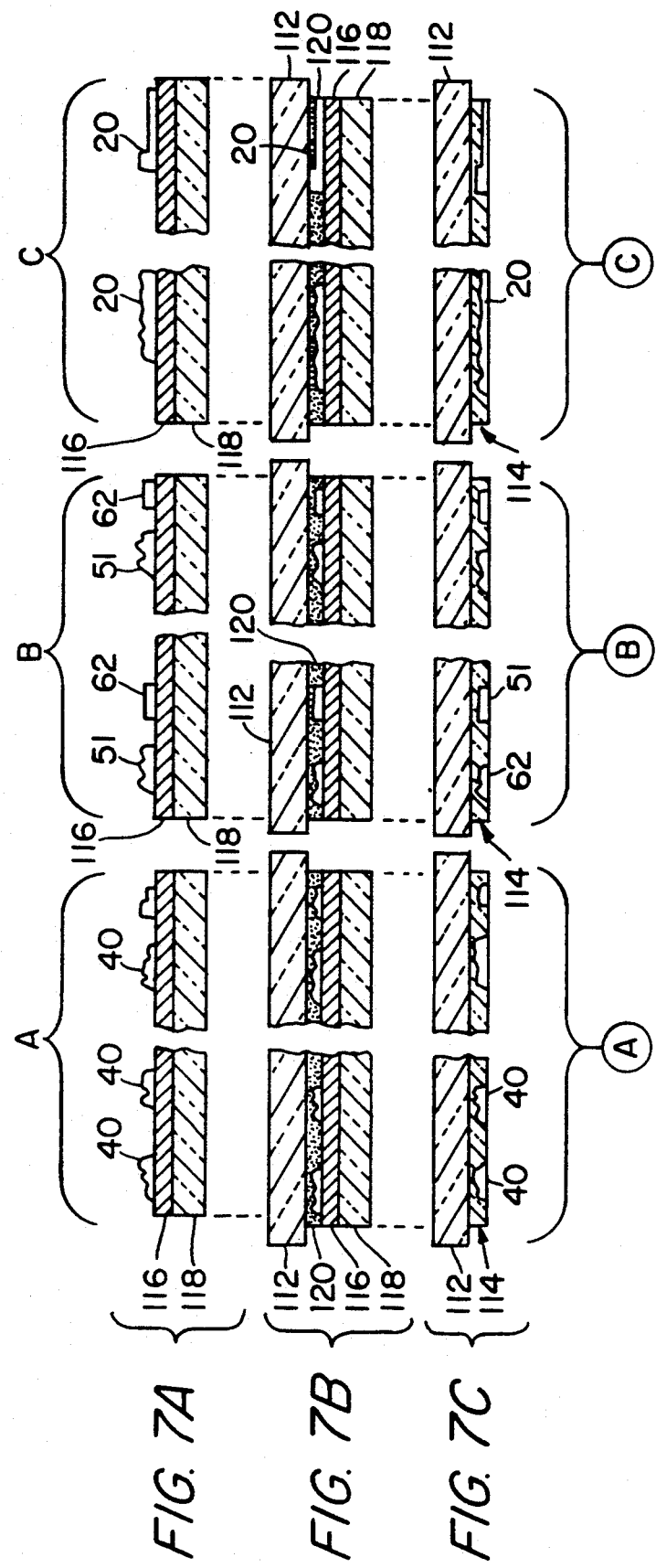

METHOD FOR MANUFACTURING A SEMICONDUCTOR DEVICE USING A CIRCUIT TRANSFER FILM

Related Applications

This application is a continuation-in-part of U.S. Ser. No. 07/636,602 filed Dec. 31, 1990 entitled "Single Crystal Silicon Arrayed Devices for Display Panels" and, now U.S. Pat. No. 5,206,749; a continuation-in-part of U.S. Ser. No. 07/643,552 filed Jan. 18, 1991 for "Light Emitting Diode Bars and Arrays and Method of Making Same" both of which are incorporated herein by reference.

BACKGROUND OF THE INVENTION

The development of new portable electronic products, such as the laptop computer, is currently of great worldwide interest. Miniaturization of the various component systems (memories, displays, and so forth) for such products requires that the necessary circuits be packed in as small a volume as possible. Packing circuits into a small volume also reduces parasitic capacitance and improves signal propagation time between circuits. One approach to this requirement is to increase the scale of integration in order to obtain all of the required functions from a circuit made from a single wafer. Unfortunately, efforts to create full-wafer circuitry have encountered unacceptable yield losses owing to the large circuit size. In the specific area of active matrix displays, a similar problem results in attempting the scale-up of the display size to and beyond the 256K pixel level.

Active matrix (AM) displays generally consist of flat-panels consisting of liquid crystals or electroluminescent materials which are switched "on" and "off" by electric fields emanating from pixel electrodes charged by thin-film transistors (TFT's) co-located with each liquid crystal or electroluminescent pixel area. These AM displays are expected to supplant cathode ray tube (CRT) technology and provide a more highly defined television picture or data display. The primary advantage of the active matrix approach, using TFT's, is the elimination of cross-talk between pixels, and the excellent grey scale that can be attained with TFT-compatible liquid crystal displays (LCD's).

Flat panel displays employing LCD's generally include five different layers: a white light source layer, a first polarizing filter layer that is mounted on one side of a circuit panel on which the TFT's are arrayed to form pixels, a filter plate layer containing at least three primary colors arranged into pixels, and finally a second polarizing filter layer. A volume between the circuit panel and the filter plate is filled with a liquid crystal material. This material rotates the polarization of light passing through it when an electric field from a pixel electrode is applied across it between the circuit panel and a ground affixed to the filter plate. Thus, when a particular pixel electrode of the display is charged up by an associated TFT, the liquid crystal material rotates polarized light being transmitted through the material so that it will pass through the second polarizing filter and be seen by the viewer.

The primary approach to TFT formation over the large areas required for flat panel displays has involved the use of films of amorphous silicon which has previously been developed for large-area photovoltaic devices. Although the TFT approach has proven to be feasible, the use of amorphous silicon compromises certain aspects of the panel performance. For example, amorphous silicon TFT's lack the frequency response needed for large area displays due to the low electron mobility inherent in amorphous material. Thus, the use of amorphous silicon limits display speed, and is also unsuitable for the fast logic needed to drive the display.

Owing to the limitations of amorphous silicon, other alternative materials are being considered, such as, polycrystalline silicon, or laser recrystallized silicon. Thin films, less than about 0.4 microns, of these materials are usually formed on glass which generally restricts further circuit processing to low temperatures.

The formation of large active-matrix displays is hampered by the unavailability of large-area single crystal Si material. Thus the conventional approach is to use thin-film amorphous (a-Si) or polycrystalline Si (poly-Si) wafers. The required number of thin-film transistors (TFT's), combined with the large number of driver circuits and the thin-film material defects inherent in a-Si or poly-Si, leads to unacceptable yield and quality problems when the entire display is to be fabricated as a unit.

A need exists, therefore, for a relatively inexpensive way to reliably form hybrid high density electronic circuits, including active matrices, memories, and other devices, in a modular approach that permits small high-quality parts or circuits to be assembled into complete large-area high-quality complex devices.

SUMMARY OF THE INVENTION

The present invention comprises a method, and resulting apparatus, for fabricating complex hybrid multifunction circuitry on a common module body, such as a substrate or superstrate, by using silicon thin film transfer processes to remove areas or tiles of circuits, formed in Si thin-films, and transferring, locating and adhering the removed tiles to a common module body. The removal of areas or tiles is hereinafter referred to, generally, as "dicing." The process of transferring, locating and adhering is generally referred to as "tiling."

The films may be formed of a-Si, poly-Si, or x-Si depending upon the desired circuit parameters. Elements of one circuit are then interconnected to elements of another circuit by conventional photolithographically patterned thin film metallization techniques. Direct laser writing or erasing may be used for repair or modification of interconnects.

The transfer may be accomplished in either of two ways—single transfer or double transfer. In the single transfer process, the desired Si circuitry is formed on a thin film Si substrate; the Si circuits are diced, i.e., divided into dice or tiles containing one or more circuits; the dice or tiles are then tiled, i.e., sequentially registered onto a common module body and sequentially adhered to the module body. After all the dice or tiles are adhered, all the Si substrates are removed in one process and the circuits interconnected. Alternately, the Si substrates may be sequentially removed if more precise alignment is required.

In the double transfer process, the circuits are transferred to an intermediary transfer or carrier body and then the substrates are removed. Dicing may occur before or after the first transferral. The thin film circuitry is supported by the transfer body until transfer to the common module body is appropriate. The circuitry is then tiled, i.e., sequentially transferred, registered and adhered to the common module body. If the transfer body is sufficiently thin, the transfer body may be left on the circuitry. If not, it is removed and circuit interconnections made, as required.

In a preferred embodiment, the common module forms an active matrix (AM) LCD panel fabricated in accordance with the invention. The circuit panel for the AMLCD, is formed by transferring to a common module substrate or superstrate, multiple x-Si and/or a-Si or poly-Si thin film tiles upon which circuits may have been formed, and wherein each tile is obtained as a unit from one or more wafers. During transfer, the tiles are registered with respect to one another. Circuits are then interconnected as necessary. Registration is accomplished by well-known X-Y micropositioning equipment. Adherence and planarity are achieved using optically transparent adhesives which fill in voids left in forming circuitry. Trimming of substrate edges may be required to obtain precise circuit dimensions needed for proper alignment on the module body.

BRIEF DESCRIPTION OF THE DRAWINGS

FIGS. 7A–7D are a process flow sequence illustrating transfer and bonding of a silicon an oxide (SOI) structure to a glass superstrate and removal of the substrate.

DETAILED DESCRIPTION OF THE INVENTION

I. Tiled Active Matrix Liquid Crystal Display

Figure 1:
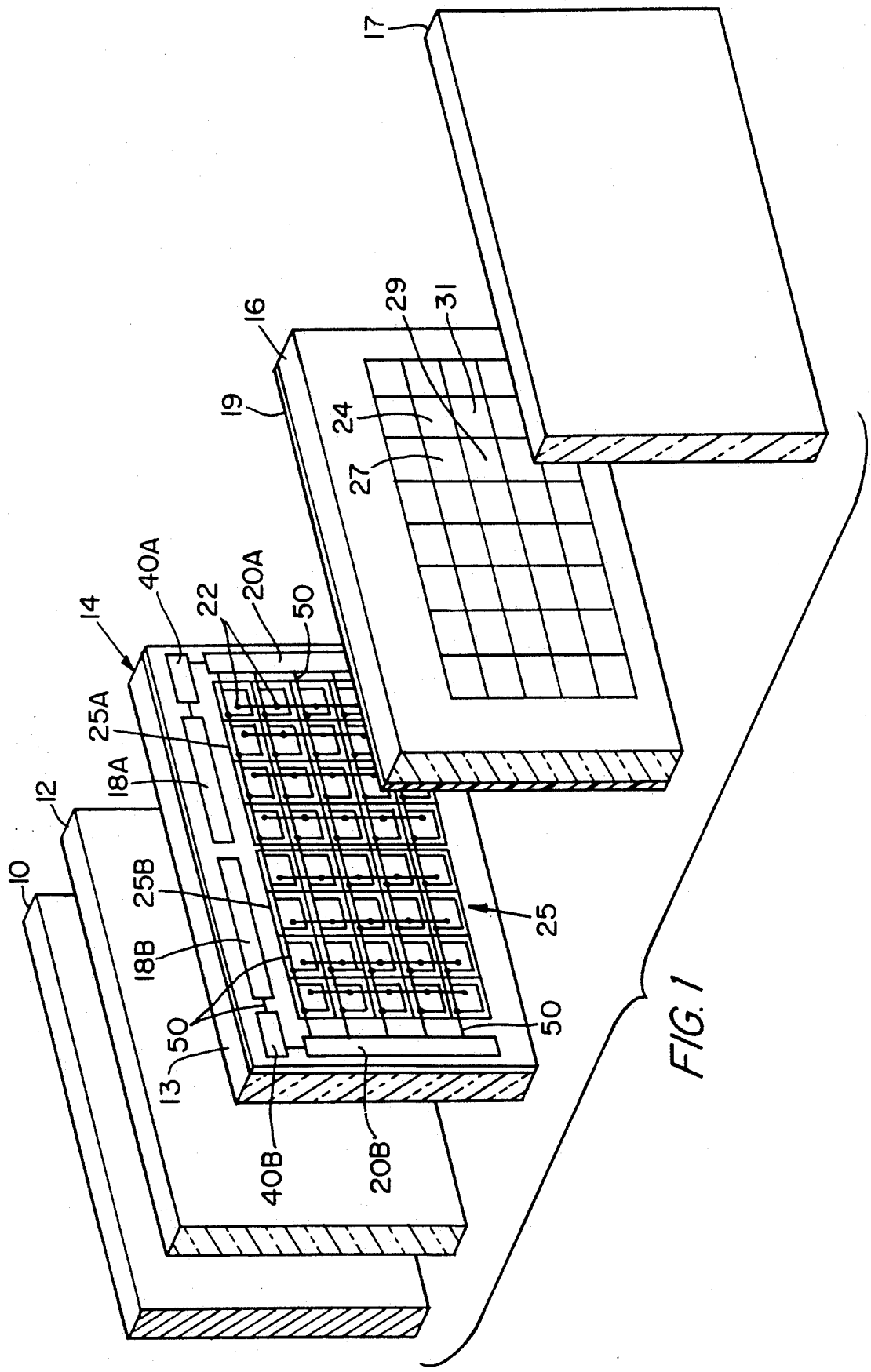
FIG. 1 is a perspective view of a high density circuit module in the form of an active matrix liquid crystal display (AMLCD).

A preferred embodiment of the invention for fabricating complex hybrid multi-function circuitry on common module substrates is illustrated in the context of an AMLCD, as shown in FIG. 1. The basic components of the AMLCD comprise a light source 10, such as a flat fluorescent or incandescent white lamp, or an electroluminescent lamp having white, or red, blue and green phosphors, a first polarizing filter 12, a circuit panel 14, an optional filter plate 16 and a second polarizing filter 17, which form a layered structure. Note: Filter plate 16 is not needed for a black and white display or where the red, green and blue colors are provided by the lamp at the appropriate pixel. A liquid crystal material 23, such as a twisted nematic is placed between the circuit panel 14 and the filter plate 16.

Figure 2A:
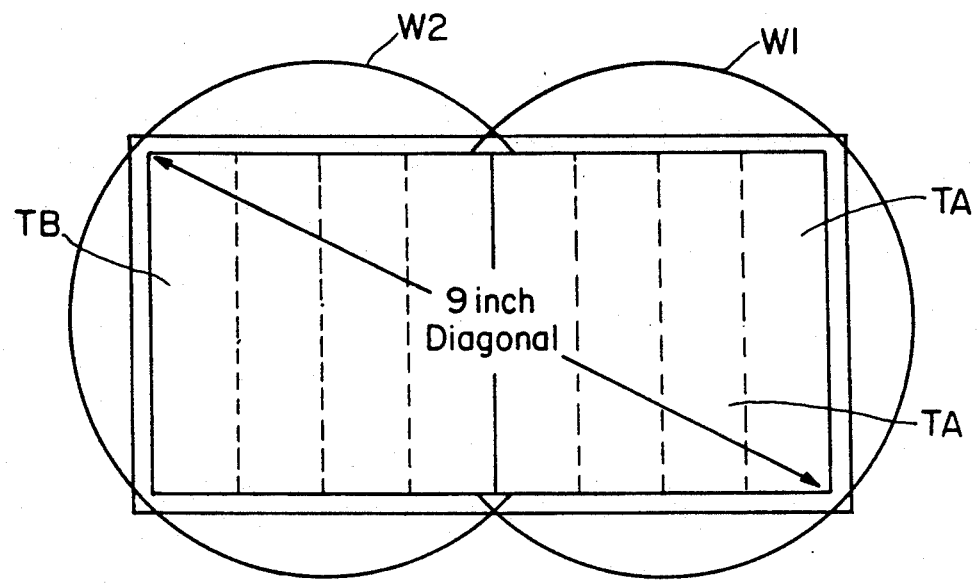
FIG. 2A is a schematic illustrating how two six inch wafers can be used to form tiles for a 4×8 inch AMLCD.
Figure 2B:
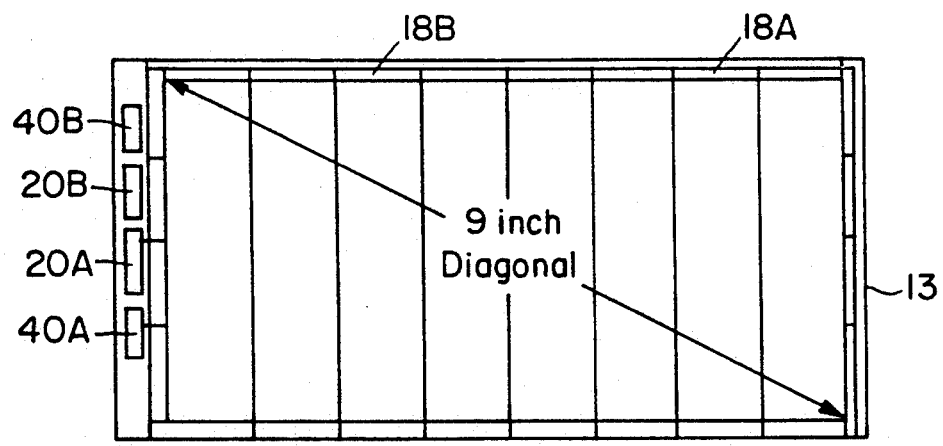
FIG. 2B shows the tiles of FIG. 2A applied to a glass substrate for forming an AMLCD.

Circuit panel 14 consists of a transparent common module body 13 formed, for example, of glass upon which is transferred a plurality of common multifunction circuits comprising control logic circuits 40A and 40B and drive circuits 18A and 18B, 20A and 20B, and array circuit 25A and 25B. Preferably, the logic and drive circuits which require high speed operation are formed in tiles of x-Si. The array circuits may be formed in a-Si material, or poly-Si, or preferably in x-Si, to achieve lower leakage in the resultant TFT's and, hence, better grey scale. Higher speed is also achieved in x-Si. A 4×8 inch active matrix LCD array can be formed from two standard 6-inch diameter Si wafers W1 and W2 as shown in FIG. 2A. Array circuit 25A is formed on wafer W1 and 1-inch by 4-inch tiles TA are transferred from the wafer W1 to the substrate 14. Note: The transfer may be accomplished using either a single or double transfer process, as will be described in detail below. Each tile is registered against another using micropositioning equipment and manipulators capable of micron scale accuracy. Similarly, tiles TB are transferred from wafer W2 to form array 25B on substrate or common module body 13 (See FIG. 2B).

Logic circuits 40A and 40B and drive circuits 18A, 18B, 20A, 20B are formed on other suitable substrates (not shown) and tiled and transferred in like manner to common substrate 13 and registered opposite the arrays 25A, 25B, as shown in FIG. 1. Conductive interconnections 50 are then made between the drive circuits and the individual pixels 22 and the logic control circuits 40A and 40B. In this manner, a 1280 by 1024 addressable array of pixels 22 are formed on the substrate 13 of circuit panel 14. Each pixel 22 is actuated by voltage from a respective drive circuit 18A or B on the X-axis and 20A or B on the Y-axis. The X and Y drive circuits are controlled by signals from control logic circuits 40A and B. Each pixel 19 produces an electric field in the liquid crystal material 23 disposed between the pixel and a counterelectrode (not shown) formed on the back side of the color filter plate 16.

The electric field formed by pixels 22 causes a rotation of the polarization of light being transmitted across the liquid crystal material that results in an adjacent color filter element being illuminated. The color filters of filter plate system 16 are arranged into groups of four filter elements, such as blue 24, green 31, red 27, and white 29. The pixels associated with filter elements can be selectively actuated to provide any desired color for that pixel group.

Figure 3:
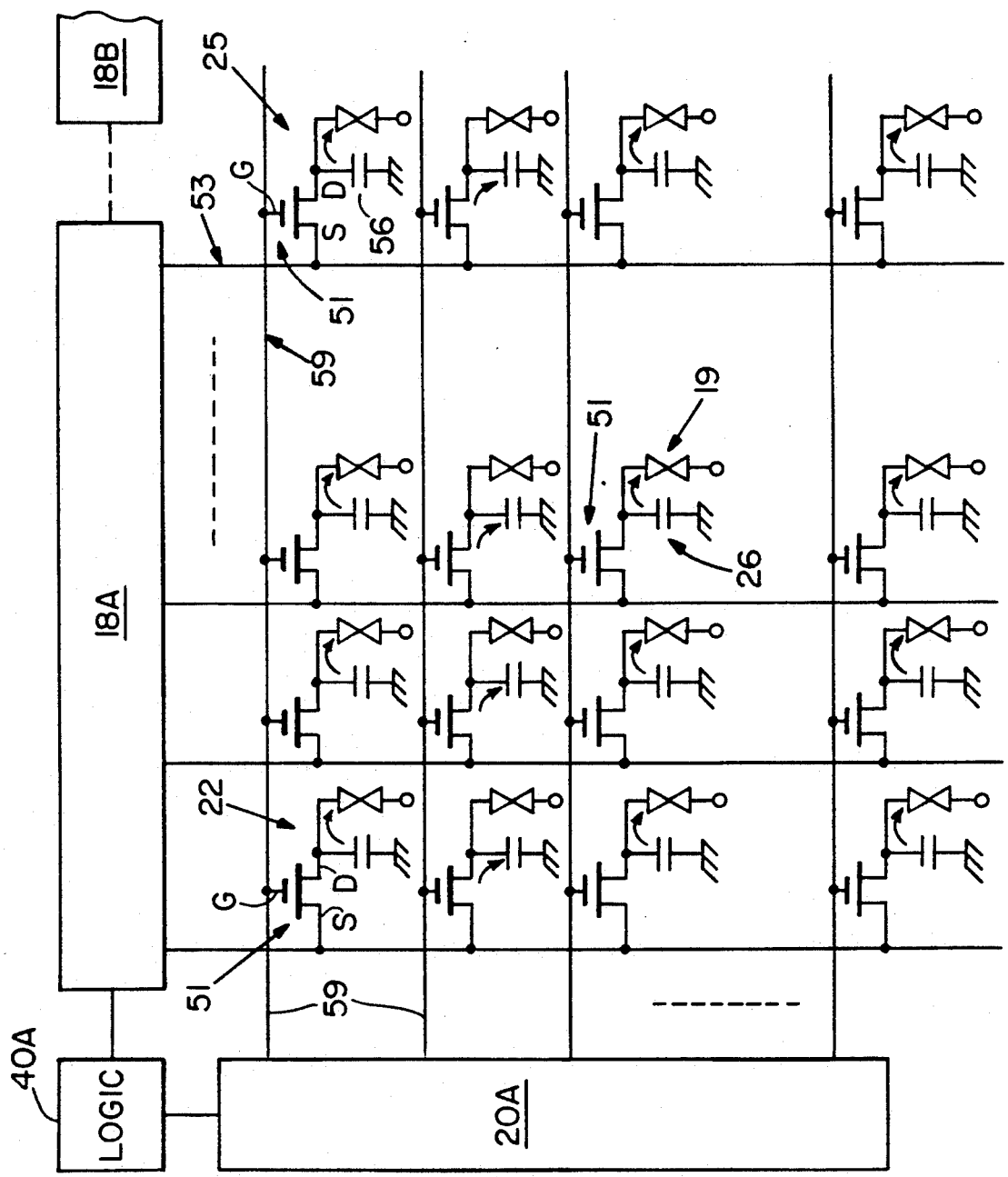
FIG. 3 is a circuit diagram illustrating the driver system for the AMLCD of FIG. 1.

A typical drive and logic circuit that can be used to control the array pixels 22 is illustrated in FIG. 3. Drive circuit 18A receives an incoming signal from control logic 40A and sends a signal to each source electrode of a TFT 51 in one of the columns selected by logic circuit 40A through interconnect buss 53. Y-drive circuit 20A controlled by logic circuit 40A energizes a row buss 59 extending perpendicular to column buss 53 and applies a voltage pulse to each gate G of TFT's 51 in a selected row. When a TFT has a voltage pulse on both its gate and source electrode current flows through an individual transistor 51, which charges capacitor 56 in a respective pixel 22. The capacitor 56 sustains a charge on the pixel electrode adjacent to the liquid crystal material (shown schematically at 19) until the next scan of the pixel array 25. Note: The various embodiments of the invention may, or may not, utilize capacitors 56 with each pixel depending upon the type of display desired.

II. Transfer Processes

The array circuits 25A and 25B and logic 40A,40B and drive circuits 18A,18B may be formed and transferred by a number of processes. The basic steps in a single transfer process are: forming of a plurality of thin film Si circuits on Si substrates, dicing the thin film to form tiles, and transferring the tiles to a common module substrate by "tiling." Tiling involves the steps of transferring, registering the transferred tiles, and adhering the registered tiles. The Si substrates are then removed and the circuits on the tiles are interconnected.

The double transfer approach, described in detail below in connection with FIGS. 4A–4L is similar except that the Si-substrate is removed after dicing and the thin film is transferred to an intermediate transfer body or carrier before ultimate transfer to the common module body.

Assuming an Isolated Silicon Epitaxy (ISE) process is used, the first step is to form a thin-film precursor structure of silicon-on-insulator (SOI) film. An SOI structure, such as that shown in FIG. 4A, includes a substrate 32 of Si, a buffer layer 30, of semi-insulating Si and an oxide 34 (such as, for example, $SiO_2$) that is grown or deposited on buffer layer 30, usually by Chemical Vapor Deposition (CVD). An optional release layer 36 of material which etches slower than the underlying oxide layer 34 is then formed over the oxide 34.

For example, a silicon oxy-nitride release layer, comprising a mixture of silicon nitride ($Si_3N_4$) and silicon dioxide ($SiO_2$) may be a suitable choice. Such a layer etches more slowly in hydrofluoric acid than does $SiO_2$ alone. This etch rate can be controlled by adjusting the ratio of N and O in the silicon oxy-nitride ($SiO_xN_y$) compound.

A thin essentially single crystal layer 38 of silicon is then formed over the release layer 36. The oxide (or insulator) 34 is thus buried beneath the Si surface layer. For the case of ISE SOI structures, the top layer is essentially single-crystal recrystallized silicon, from which CMOS circuits can be fabricated.

Note: for the purposes of the present application, the term "essentially" single crystal means a film in which a majority of crystals show a common crystalline orientation and extend over a cross-sectional area in a plane of the film for at least 0.1 $cm^2$, and preferably, in the range of 0.5–1.0 $cm^2$, or more. The term also includes completely single crystal Si.

The use of a buried insulator provides devices having higher speeds than can be obtained in conventional bulk (Czochralski) material. Circuits containing in excess of 1.5 million CMOS transistors have been successfully fabricated in ISE material. An optional capping layer (not shown) also of silicon nitride may also be formed over layer 36 and removed when active devices are formed.

Figure 4A:
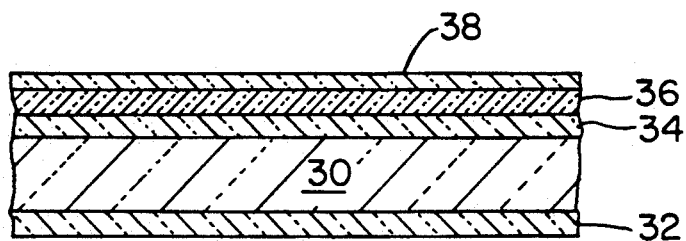
FIGS. 4A–4L are a preferred process flow sequence illustrating the fabrication of the a portion of the circuit panel for the AMLCD of FIG. 1.
Figure 4B:
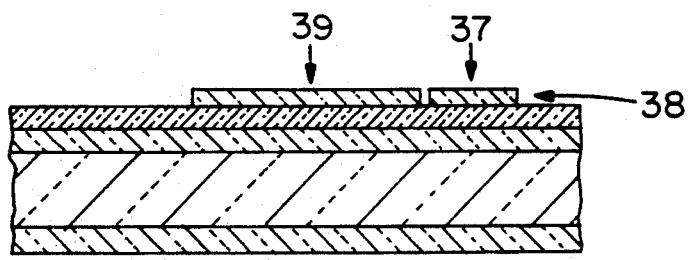
Figure 4C:
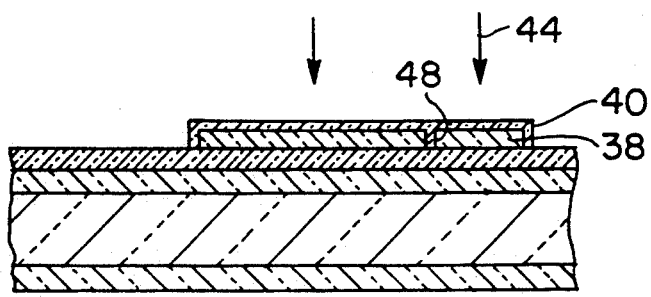

As shown in FIG. 4B. the film 38 is patterned to define active circuits, such as a TFT's in region 37 and a pixel electrode region at 39 for each display pixel. Note: For simplification, only one TFT 51 and one pixel electrode 62 is illustrated (FIG. 4H). It should be understood that an array of 1280 by 1024 such elements can in practice be formed on a single 6-inch wafer.

A plurality of arrays may be formed on a single six-inch wafer, which are then applied to the display as tiles and interconnected. Alternatively, the plurality of pixel matrices from one wafer can be separated and used in different displays. The plurality may comprise one large rectangular array surrounded by several smaller arrays (to be used in smaller displays). By mixing rectangular arrays of different areas, such an arrangement makes better use of the total available area on a round wafer.

An oxide layer 40 is then formed over the patterned regions including an insulator region 48 formed between the two regions 37, 39 of each pixel. The intrinsic crystallized material 38 is then implanted 44 (at FIG. 4C) with boron or other p-type dopants to provide a n-channel device (or alternatively, an n-type dopant for a p-channel device).

Figure 4D:
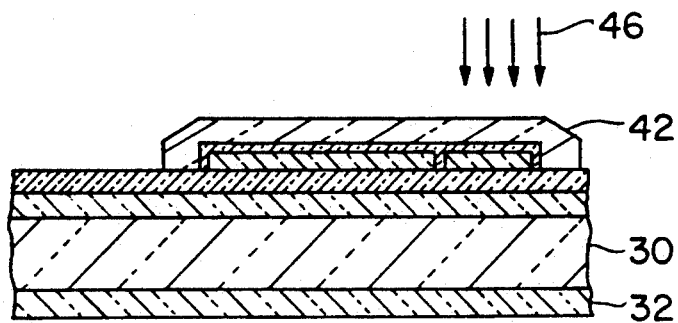
Figure 4E:
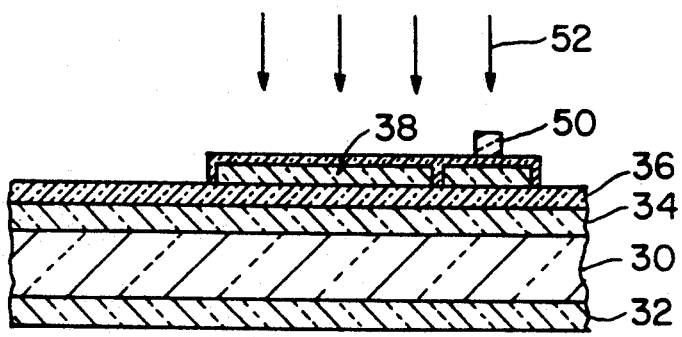
Figure 4F:
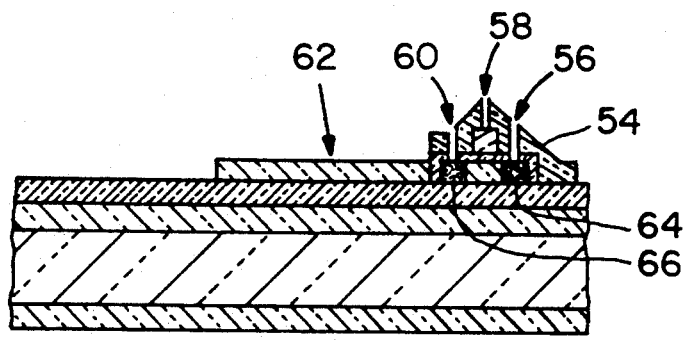
Figure 4G:
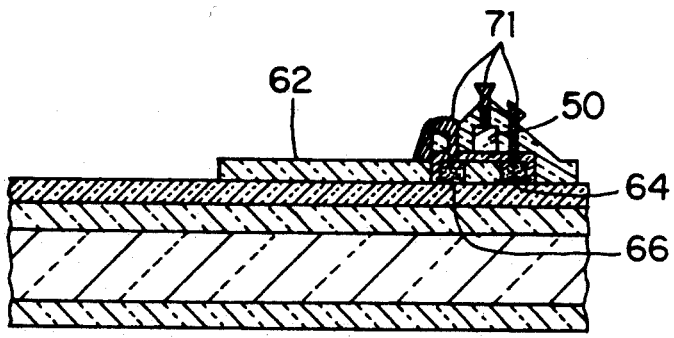
Figure 4H:
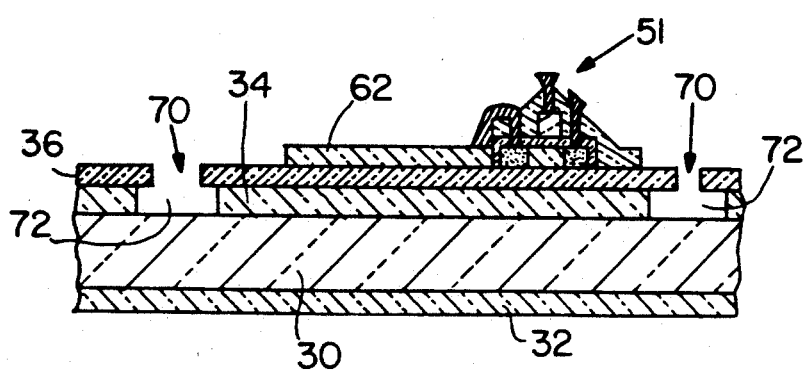

A polycrystalline silicon layer 42 is then deposited over the pixel and the layer 42 is then implanted 46, through a mask as seen in FIG. 4D, with an n-type dopant to lower the resistivity of the layer 42 to be used as the gate of the TFT. Next, the polysilicon 42 is patterned to form a gate 50, as seen in FIG. 4E, which is followed by a large implant 52 of boron to provide p+ source and drain regions 66, 64 for the TFT on either side of the gate electrode. As shown in FIG. 4F, an oxide 54 is formed over the transistor and openings 60, 56, 58 are formed through the oxide 54 to contact the source 66, the drain 64, and the gate 50. A patterned metallization 71 of aluminum, tungsten or other suitable metal is used to connect the exposed pixel electrode 62 to the source 66 (or drain), and to connect the gate and drain to other circuit panel components.

The devices have now been processed and the circuits may now be tested and repaired, as required, before further processing occurs.

The next step in the process is to transfer the silicon pixel circuit film to a common module, either directly, or by a double transfer from substrate to carrier and then to the common module. A double transfer approach is illustrated in FIGS. 4H–4L. To separate a circuit tile from the buffer 30 and substrate 37, a first opening 70 (in FIG. 4H) is etched in an exposed region of release layer 36 that occurs between tiles. Oxide layer 34 etches more rapidly in HF than nitride layer 36, thus a larger portion of layer 34 is removed to form cavity 72. A portion of layer 36 thus extends over the cavity 72.

Figure 4I:
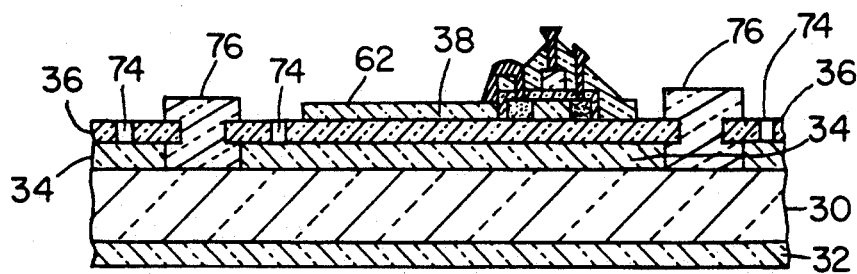
Figure 4J:
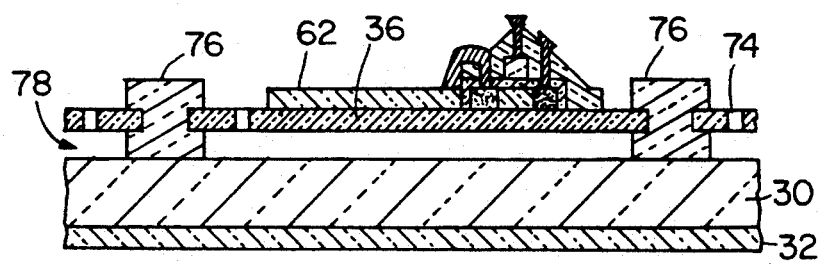
Figure 4K:
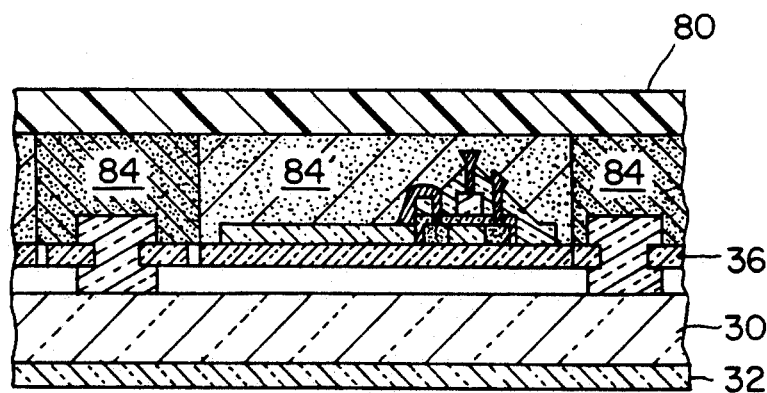
Figure 4L:
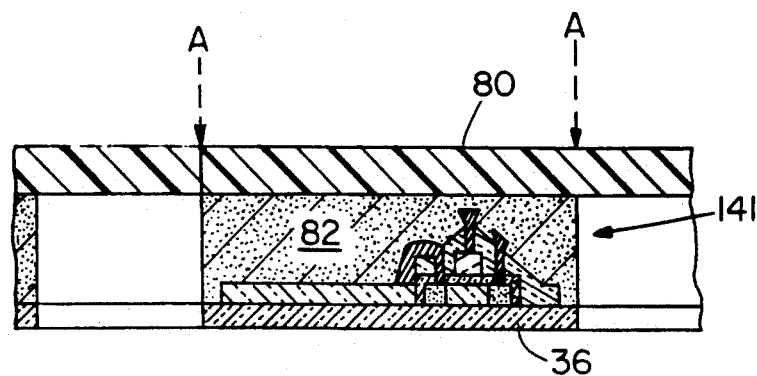

In FIG. 4I, a support post 76 of oxide is formed to fill cavity 72 and opening 70, which extends over a portion of layer 36. Openings or via holes 74 are then provided through layer 36 such that an etchant can be introduced through holes 74, or through openings 78 etched beneath the release layer 36, to remove layer 34 (See FIG. 4J). The remaining release layer 36 and the circuitry supported thereon is now held in place relative to substrate 32 and buffer 30 with support posts 76.

Next, an epoxy 84 that can be cured with ultraviolet light is used to attach an optically transmissive superstrate 80 to the circuitry, and layer 36. The buffer 30 and substrate 32 is then patterned and selectively exposed to light such that regions of epoxy 84' about the posts 76 remain uncured while the remaining epoxy 84' is cured (See FIG. 4K). The buffer 30 and substrate 32 and posts 76 are removed by cleavage of the oxide post and dissolution of the uncured 84 epoxy to provide the thin film tile structure 141, shown in FIG. 4L mounted on carrier 80.

To form the final display panel, the edges of the carrier 80 are trimmed to coincide with the tile borders. The nitride release layer 36 is removed by etching.

Figure 5A:
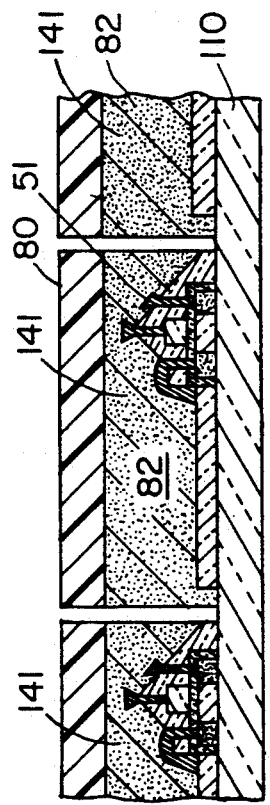
FIGS. 5A and 5B are cross-sectional schematic process views of a portion of the AMLCD.
Figure 5B:
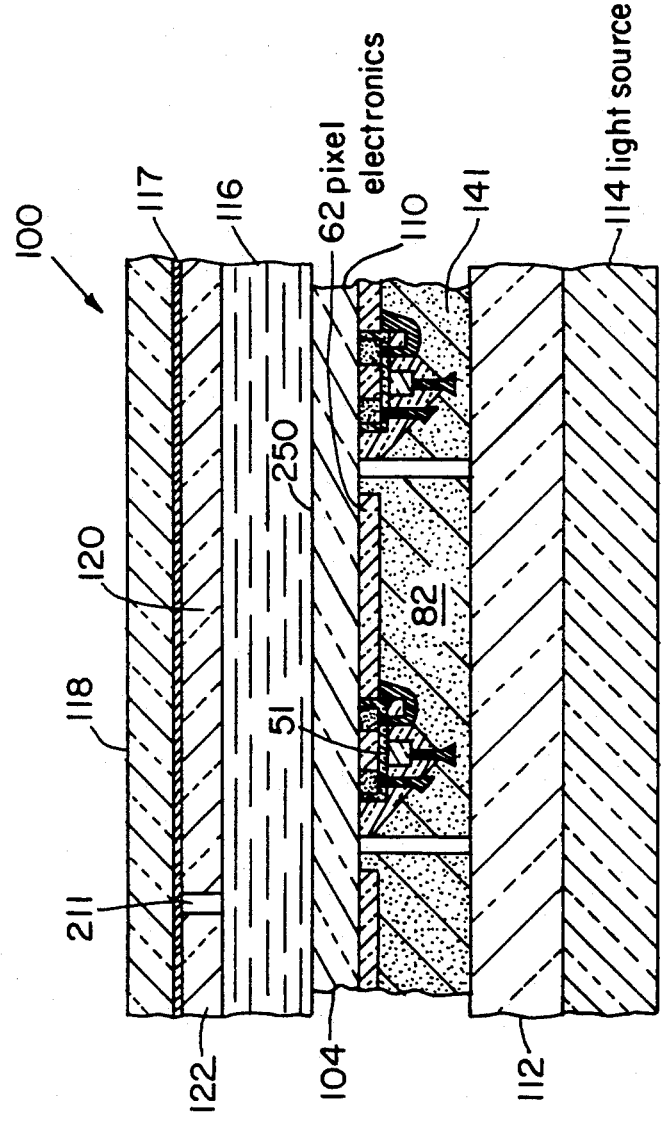

As shown in FIG. 5A, a plurality of tile structures 141 are then sequentially registered with one another and adhered to a common module body 110 using a suitable adhesive (not shown). Common module body 110 is preferably patterned with interconnect metallization on the surface facing the tile structure 141 for interconnecting individual tile circuitry with each other. Next, insulation and alignment layers, spacers, a sealing border and bonding pads for connections (not shown) are bonded onto the periphery of the common module body 110. A screen printing process can be used to prepare the border. As shown in FIG. 5B, a plate 117 containing the color filters 120 and the counterelectrode (not shown) is bonded to the peripheral thin film circuit tiles 141 with the sealing border after insertion of spacers (not shown). The display is filled with the selected liquid crystal material 116 via a small filling hole or holes extending through the border. This filling hole is then sealed with a resin or epoxy. First and second polarizer films 118, 112 or layers are then bonded to both sides and connectors (not shown) are added. Finally, a white light source 114, or other suitable light source, is bonded to polarizer 112.

Pixel electrodes 62 are laterally spaced from each other. Each pixel has a transistor 51 and a color filter 120 or 122 associated therewith. A bonding element or adhesive 82 and optically transmissive superstrate 110, such as glass or plastic completes the structure. Body 110 is preferably a low temperature glass that can have a thickness preferably of about 200 to 1000 microns.

In an alternative CLEFT process, thin single-crystal films, are grown by chemical vapor deposition (CVD), and separated from a reusable homoepitaxial substrate.

The films removed from the substrate by CLEFT are "essentially" single-crystal, of low defect density, are only a few microns thick, and consequently, circuit panels formed by this process have little weight and good light transmission characteristics.

The CLEFT process, illustrated in U.S. Pat. No. 4,727,047, involves the following steps: growth of the desired thin film over a release layer (a plane of weakness), formation of metallization and other coatings, formation of a bond between the film and a second substrate, such as glass (or superstrate), and separation along the built-in-plane of weakness by cleaving. The substrate is then available for reuse.

The CLEFT process is used to form sheets of essentially single crystal material using lateral epitaxial growth to form a continuous film on top of a release layer. For silicon, the lateral epitaxy is accomplished either by selective CVD or, preferably, the ISE process or other recrystallization procedures. Alternatively, other standard deposition techniques can be used to form the necessary thin film of essentially single crystal material.

One of the necessary properties of the material that forms the release layer is the lack of adhesion between the layer and the semiconductor film. When a weak plane has been created by the release layer, the film can be cleaved from the substrate without any degradation. As noted in connection with FIGS. 4A-4C, the release layers can comprise multi-layer films of $Si_3N_4$ and $SiO_2$. Such an approach permits the $SiO_2$ to be used to passivate the back of the CMOS logic. (The $Si_3N_4$ is the layer that is dissolved to produce the plane of weakness.) In the CLEFT approach, the circuits are first bonded to the glass, or other transfer substrate, and then separated, resulting in simpler handling as compared to, for example, UV-cured tape.

In the ISE process, the oxide film is strongly attached to the substrate and to the top Si film which will contain the circuits. For this reason, it is necessary to reduce the strength of the bond chemically. This requires use of a release layer that is preferentially dissolved with an etchant without complete separation to form a plane of weakness in the release layer. The films can then be separated mechanically after the glass is bonded to the circuits and electrodes.

Mechanical separation may be accomplished by bonding the upper surface of the Si film to a superstrate, such as glass, using a transparent epoxy. The film and glass are then bonded with wax to glass plates about 5 mm thick that serve as cleaving supports. A metal wedge is inserted between the two glass plates to force the surfaces apart. Since the mask has low adhesion to the substrate, the film is cleaved from the substrate but remains mounted on the glass. The substrate can then be used for another cycle of the CLEFT process, and the device processing may then be completed on the back surface of the film. Note that since the device remains attached to a superstrate, the back side can be subjected to standard wafer processing, including photolithography.

Figure 6:
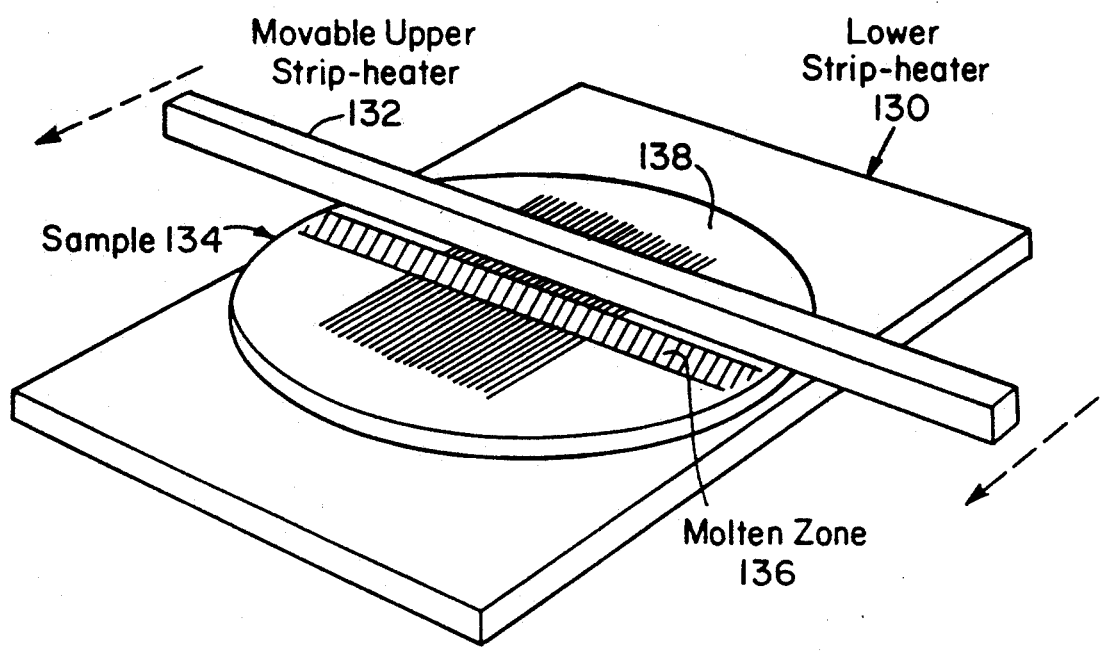
FIG. 6 illustrates in a perspective view a preferred embodiment of a system used for recrystallization.

One embodiment of the invention utilizes a recrystallization system, shown schematically in FIG. 6 to form the essentially single crystal Si thin film. A sample wafer 134 is formed of poly Si, formed on $SiO_2$, formed on an Si wafer. A capping layer 138 is formed over the poly Si. The wafer temperature is then elevated to near the melting point by a lower heater 130. An upper wire or graphite strip heater 132 is then scanned across the top of the sample 134 to cause a moving melt zone 136 to recrystallize or further crystallize the polycrystalline silicon. The lateral epitaxy is seeded from small openings formed through the lower oxide. The resultant single crystal film has the orientation of the substrate.

III. Alternate Adhesion and Transfer Processes

Figure 7D:
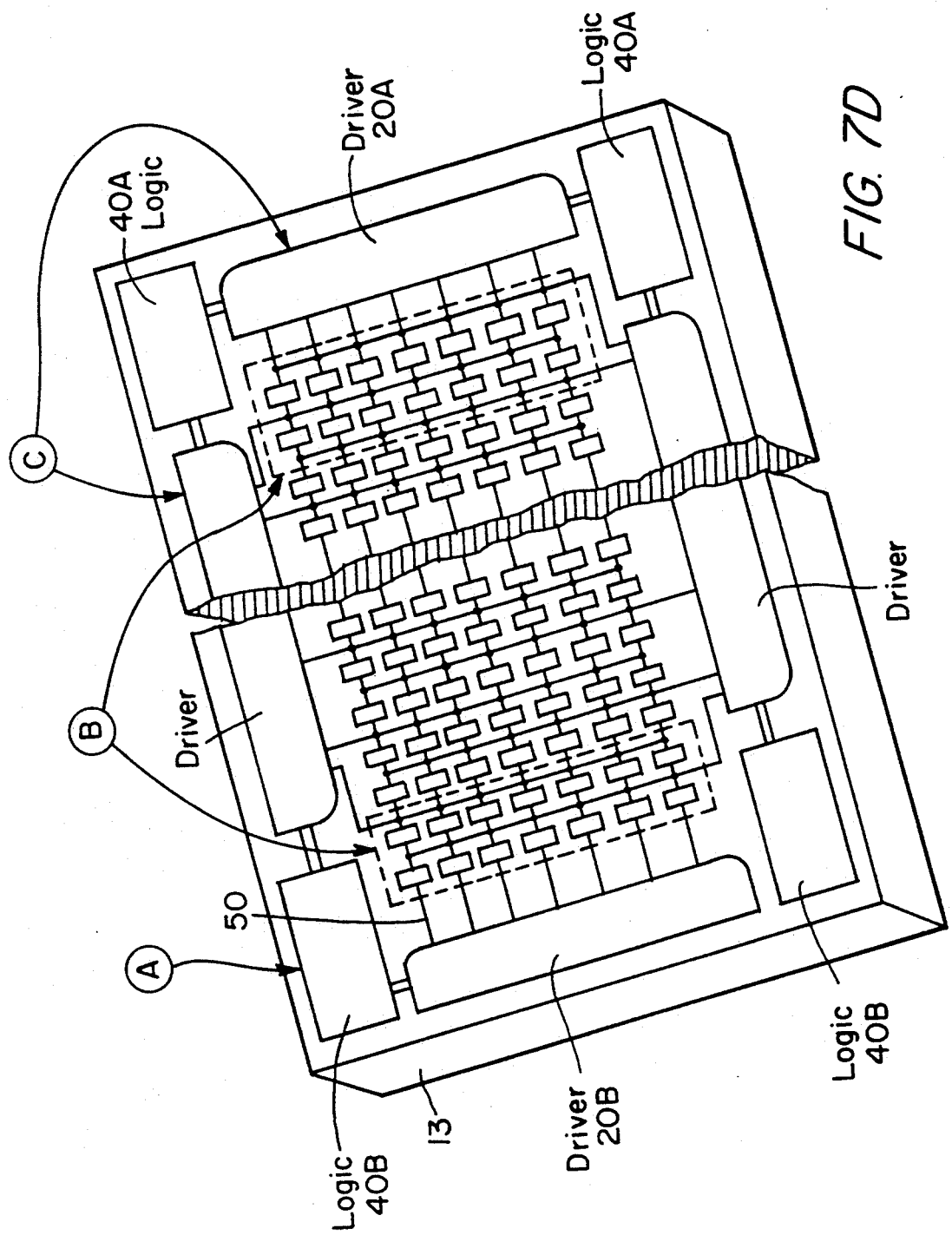

FIGS. 7A and 7D illustrate an alternate preferred double transfer process for adhering and transferring tiles of circuits of thin films of silicon to a common module body. The starting structure is a silicon wafer 118 upon which an oxide layer 116 and a thin film of poly-Si, $\alpha$-Si or x-Si 114 is formed using any of the previously described processes such as ISE or CLEFT. A plurality of circuits, such as pixel electrodes, TFT's, Si drivers and Si logic circuits, are then formed in the thin film. FIG. 7A shows three such wafers, I, II, III. In wafer I, logic circuits 40 are formed. In wafer II, pixel electrodes 62 and TFT's 51 are formed. In wafer III, driver circuits 20 are formed. A wafer, or individual tiles diced from the wafer, is attached to a superstrate transfer body 112, such as glass or other transparent insulator, using an adhesive 120. Preferably the adhesive is comprised of an epoxy, such as, a cycloaliphatic anhydride; for example, "EP-112" made by Masterbond Inc. The adhesive must satisfy the following criteria:
Excellent spectral transmission in the visible range;
Good adhesion to glass, oxides, metals, nitrides;
No reactions with glass, metals, oxides, nitrides;
Low shrinkage;
Low warp/stress;
Able to tolerate acids at 100° C. for extended periods without lifting, losing adhesion, or degrading;
Able to withstand 180° C. for 2 hours with no optical change;
Good resistance to acids and solvents;

Able to tolerate dicing and heating steps (including an acid etch step with no lifting);
Low viscosity to allow thin adhesive films; and
Ability to be vacuum degassed to eliminate all bubbles.

In general, the cycloaliphatic anhydrides meet most of the above criteria. The epoxy preferably has a low cure temperature to minimize shrinkage, a very low ion content (<5 ppm) and spectral stability over extended time periods.

The wafer, or tile, 230 is attached, using the adhesive 120, to a glass superstrate 112. The adhesive is vacuum degassed to eliminate all bubbles. The sandwich structure is then cured at a low temperature of about 100° C. for 4-8 hours which causes the adhesive to gel and minimizes the shrinkage characteristics. Then the adhesive is fully cured at a higher temperature of about 160° C. for about 8 hours. This cure assures that the bonds are fully matured. Without this cure, the adhesive will not stand up to the subsequent acid etching step.

The wafer, or tile, is then cleaned and the native oxide 118 is etched off the back surface. The wafer is put into a solution (KOH or equivalent) of 25 grams to 75 ml $H_2O$ at 100° C. Depending on the thickness of the wafer, it may take up to 5 hours to etch the Si 118. The solution etches silicon very rapidly, i.e. 2 to 3 microns/min., and uniformly if the wafers are held horizontally in the solution with the etching surface face up. The acid has a very low etch rate on oxide, so that as the substrate is etched away and the buried oxide is exposed, the etching rate goes down. The selectivity of the silicon etch rate in KOH versus the oxide etch rate in KOH is very high (200:1). This selectivity, combined with the uniformity of the silicon etching, allows the observer to monitor the process and to stop the etch in the buried oxide layer 116' without punching through to the thin silicon layer 114 above it. Wafers up to 25 mils thick and oxides as thin as 4000 Å have been successfully etched using this process. An alternative etchant is hydrazine, which has a much higher etch rate selectivity or ethylene diamine pyrocatacol (EDP).

When the silicon is completely gone, the vigorous bubbling, which is characteristic of silicon etching in KOH, abruptly stops, signalling that the etching is complete.

The thin films 114 transferred to the respective glass superstrates 112 are now rinsed and dried. If not already provided with circuits 40, 51, 62 or 20, the films 114 can be backside circuit processed, if desired, since the epoxy adhesive 120 has very good resistance to chemicals. In addition, the epoxy is very low in stress, so that the thin film is very flat and can go through conventional photolithography steps.

After all the necessary circuits are formed, as above, on transfer bodies 112, they may now be diced and tiled onto a common module body 13 to perform a combined function, such as an AMLCD.

The logic circuits 40 of transfer body 118 in col. A, FIG. 7C, are transferred to the border of module body 13, while the driver circuits 20 from the transfer body 118 in col. C, FIG. 7C, are disposed on the border between the logic circuits 40A and 40B.

Tiles of pixel electrodes 62 and TFT's 51 are formed by dicing or etching and are registered with respect to each other and pre-formed wiring 50 on module body 13, as shown.

After all the circuits are registered and adhered to the module body, the transfer body 118 and the epoxy 120 is removed using a suitable etchant, such as HF for the case of a glass transfer body.

Interconnection of circuits is achieved during registration or by direct laser writing where necessary. Also, if desired, the film can be transferred to another substrate and the first glass superstrate and adhesive can be etched off, allowing access to the front side of the wafer for further circuit processing.

Figure 8A:
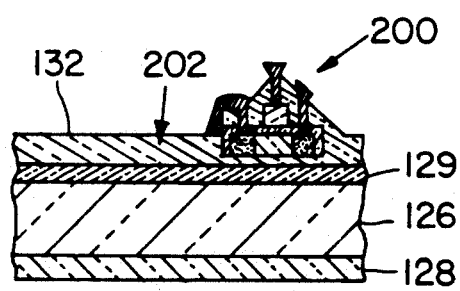
FIGS. 8A and 8B are a process flow sequence illustrating an alternative transfer process in which a GeSi alloy is used as an intermediate etch step layer.
Figure 8B:
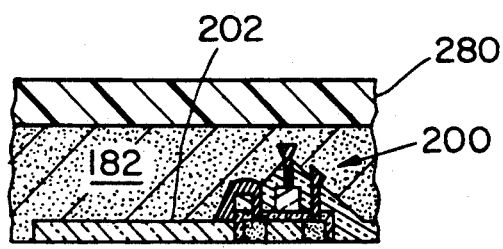

FIGS. 8A and 8B illustrate an alternative one-step silicon thin film transfer process in which GeSi is used as an intermediate etch stop layer. In this process, Si buffer layer 126 is formed on an x-Si substrate 128 followed by a thin GeSi layer 129 and a thin α-Si, poly-Si, or x-Si device or circuit layer 132; using well-known CVD or MBE growth systems.

The layer 132 is then IC processed in the manner previously described in connection with FIGS. 4E-H, to form circuits, such as TFT's 200 and pixel electrodes 202 (FIG. 8A). Next, the processed wafers, or tiles from the wafer, are mounted on a common module glass (or other) support 280 using an epoxy adhesive of the type previously mentioned in connection with FIGS. 7A-7B. The epoxy fills in the voids formed by the previous processing and adheres the front face to the superstrate 280.

Next, the original Si substrate 128 and Si buffer 126 are removed by etching with a KOH solution, which does not affect the GeSi layer 129 (FIGS. 8B). Finally, the GeSi layer 129 is removed by brief submersion in a suitable etch.

V. Pressure Sensor Embodiment

Figure 9A:
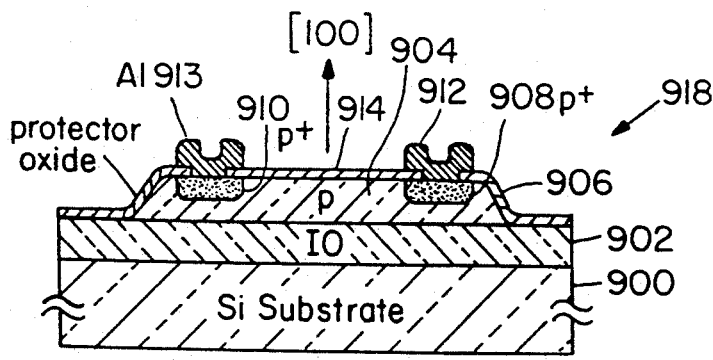
FIGS. 9A and 9B are a process flow sequence illustrating another thin film tile transfer process used to form a pressure sensor or an array of such sensors.
Figure 9B:
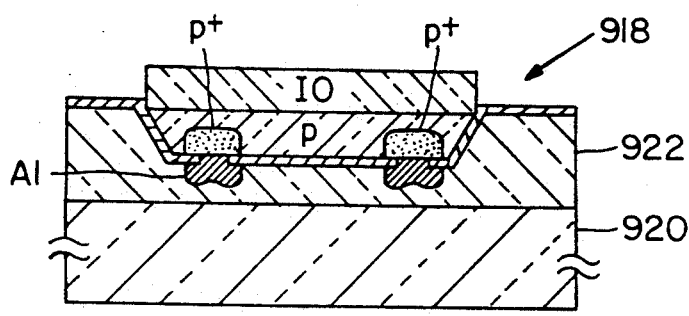

FIGS. 9A-9B illustrate an alternate embodiment of the invention wherein the transfer and adherence processes of the invention are used to mount pressure sensing transducers on a glass substrate. The starting structure is shown in FIG. 9A. An SOI wafer is provided which consists of an Si substrate 900 beneath a buried oxide layer 902, upon which is formed a single, or nearly single, crystal Si layer 904. A blanket implant of boron ions is made to make the Si layer a p-type conductor. A thin (1000 Å)blanket protective/mask layer of oxide ($SiO_2$) (not shown) is then formed over the structure. (Note FIG. 9A shows the structure after processing). Single, or nearly single, islands of χ-Si are then formed by applying photoresist over the oxide structure and etching the oxide and silicon 904 between islands to align the edges of the islands parallel to the [110] plane. Photo resist is applied again and contact openings formed to contact regions 910 and 908, which are then implanted with a high dose of boron ions to form P type conductivity regions. A protective oxide layer 906 is then formed over the island. Aluminum contact pads, 912 and 913 to the contacts 908, 910 are formed in openings provided through oxide 906.

Figure 10A:
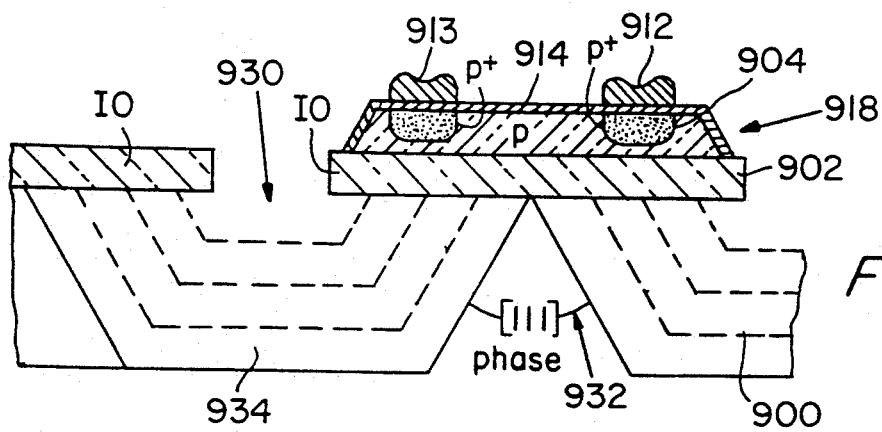
FIGS. 10A and 10B illustrate an alternate process to the process of FIGS. 9A and 9B.
Figure 10B:
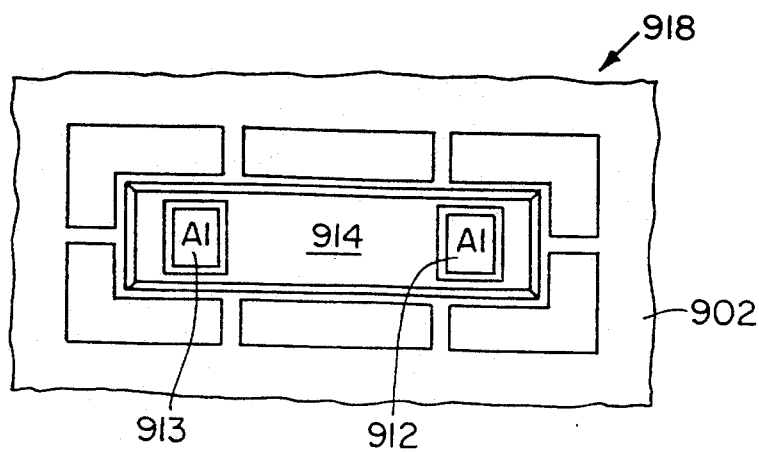

The pressure transducer circuit of FIG. 9A is now ready for transfer to a glass substrate as in FIG. 9B or to a silicon bridge as in FIGS. 10A and 10B. The transducer circuit operates by sensing a change in the resistance of the p-region 904 in response to pressure applied to the circuit. This resistance change may be sensed by an ohmmeter coupled across contacts 912 and 913 and calibrated and converted into a pressure sensor to serve as a strain gauge.

To transfer the circuit 918 to a common module glass substrate 920 the silicon substrate 900 is etched away in a KOH solution. Then using a photoresist and mask the initial oxide layer 902 is etched around the periphery of the circuit 918 leaving the circuit free to be inverted and transferred to the glass substrate 920 and releasibly bonded thereto using a removable epoxy 922 from which it can be transferred and bonded to a module for general sensing, including temperature, pressure, acceleration, and so forth, all under microprocessor supervision, to make a high speed process controller.

FIGS. 10A and 10B illustrate an alternate transfer process in which the initial oxide 902 is etched about the periphery of each circuit 918 using a conventional photoresist and mask technique. The Si substrate 900 is also etched locally using hydrazine which preferentially etches Si to reveal the [111] plane. Etching of the Si substrate with hydrazine undercuts the circuits 918 forming an upper cavity 930 between adjacent circuits and a lower wedge shaped cavity 932 beneath the center of the circuit and leaving a bridge structure 934 between circuits 918.

When it is desired to remove one or more circuits 918, a vacuum wand may be used to seize one or more circuits and break the bridge to remove the circuits which may then be transferred along with other circuits to a common module substrate and aligned and interconnected with other circuitry to perform an overall function as previously described.

FIG. 10B is a top-plan view of FIG. 10A before substrate 900 is etched.

Equivalents

Other preferred embodiments employ the use of a solid state material to form a light valve for each pixel. A light emitting material, such as an electroluminescent film or any material whose optical transmission properties can be altered by the application of an electric field, can be used to supply the light valve of the present invention.

We claim:

1. The process of forming multi-function electronic circuitry on a common body comprising the steps of:
  a) forming a plurality of first electronic circuits, for performing a first function, in a first semiconductor film formed on a first substrate;
  b) forming a plurality of second electronic circuits, for performing a second function, in a second semiconductor film formed on a second substrate;
  c) separating areas of said films of said first and second substrates to form circuit tiles;
  d) transferring said tiles to a common module body;
  e) registering the tiles on said common module body;
  f) adhering said tiles to the common module body;
  g) removing the substrates from the tiles;
  h) interconnecting first and second electronic circuits of said transferred tiles.

2. The process of claim 1 wherein the films are formed of silicon material from the group comprising amorphous Si, polysilicon or essentially single crystal silicon.

3. The process of claim 1 wherein the first circuits are thin film transistors and the second circuits are driver circuits.

4. The process of claim 1 wherein the circuits are formed in recrystallized polysilicon formed over a buried insulator and wherein the recrystallized silicon forms an essentially single crystal layer.

5. The process of claim 3 wherein the second circuits are formed in essentially single crystal silicon material and the first circuits are formed in Si from the group comprising amorphous or polysilicon material.

6. The process of claim 1 wherein the tiles are transferred sequentially and the substrates are removed sequentially.

7. The process of claim 1 wherein the first electronic circuits comprise thin film transistor circuits and the second electronic circuits comprise driver circuits and the common body is formed of a light transparent medium.

8. The process of claim 6 wherein the films are adhered using an ultra-violet light curing adhesive.

9. The process of claim 6 wherein an intermediate sacrificial layer is formed between the semiconductor film and the substrates to facilitate removal of the substrate.

10. The process of claim 7 wherein the tiles are formed using a process from the group comprising: sawing, cleaving or etching the substrates.

11. The process of forming multi-function electronic circuitry on a common body comprising the steps of:
  a) forming a plurality of first electronic circuits, for performing a first function, in a first semiconductor film formed on a first substrate;
  b) forming a plurality of second electronic circuits, for performing a second function, in a second semiconductor film formed on a second substrate;
  c) separating areas of said films of said first and second substrates to form circuit tiles and transferring said tiles to a body;
  d) removing the substrates from the tiles;
  e) transferring said circuit tiles and said body to said common body; and
  f) removing said body.

12. The process of claim 11 wherein the films are formed of silicon material from the group comprising amorphous Si, polysilicon or single crystal silicon.

13. The process of claim 11 wherein the first circuits are transistors and the second circuits are driver circuits.

14. The process of claim 11 wherein the circuits are formed in recrystallized polysilicon formed over a buried insulator and wherein the recrystallized polysilicon forms an essentially single crystal layer.

15. The process of claim 13 wherein the second circuits are formed in essentially single crystal silicon material and the first circuits are formed in Si from the group comprising amorphous or polysilicon material.

16. The process of claim 11 wherein the tiles are transferred sequentially and the substrates are removed sequentially.

17. The process of claim 11 wherein the first electronic circuits comprise thin film transistor circuits and the second electronic circuits comprise driver circuits and the common body is formed of a light transparent medium.

18. The process of claim 16 wherein the films are adhered using an ultra-violet light curing adhesive.

19. The process of claim 16 wherein an intermediate sacrificial layer is formed between the semiconductor film and the substrates to facilitate removal of the substrate.

20. The process of claim 17 wherein the tiles are formed using a process from the group comprising: sawing, cleaving or etching.

21. Apparatus for performing multiple electronic functions comprising:
  a) a common module body;

b) first tiles bonded to said body having first circuits formed therein of silicon, said first circuits having elements for performing a first electronic function;

c) second tiles bonded to said body having second circuits formed therein on thin-film silicon, said second circuits having elements for performing a second electronic function; and d) interconnection means for connecting the elements of first and second circuits.

22. The apparatus of claim 21 wherein the silicon is comprised of material from the group comprising: amorphous, poly or single crystal.

23. The apparatus of claim 21 wherein the first circuits comprise thin-film transistors and the second circuits comprise driver circuits and wherein the interconnections connect the transistors to an array driven by the driver circuits.

24. The apparatus of claim 23 wherein the common module body comprises a portion of an active matrix liquid crystal display.

25. The process of forming electronic circuitry on a common body comprising the steps of:

a) forming a plurality of first electronic circuits, for performing a first function, in a first semiconductor film formed on a first substrate;

b) separating areas of said film of said first substrate to form circuit tiles;

c) transferring said tiles to a common body; and d) removing the substrates from the tiles.

26. The process of claim 25 wherein the films are formed of material from the group comprising amorphous Si, polysilicon or essentially single crystal silicon.

27. The process of claim 26 wherein the first circuits are thin film transistors.

28. The process of forming electronic circuitry on a common body comprising the steps of:

a) forming a plurality of first electronic circuits, for performing a first function, in a first semiconductor film formed on a first substrate;

b) separating areas of said film of said first substrate to form circuit tiles and transferring said tiles to a transfer body;

c) removing the substrates from the tiles; and d) transferring said circuit tiles to said common body.

* * * * *